United States Patent
Wang et al.

(10) Patent No.: US 11,841,414 B2
(45) Date of Patent: Dec. 12, 2023

(54) RESPIRATORY DETECTION TRANSCEIVER

(71) Applicant: Siemens Healthcare GmbH, Erlangen (DE)

(72) Inventors: JianMin Wang, Shenzhen (CN); Qiu Yi Zhang, Shenzhen (CN); Markus Vester, Nuremberg (DE); Jia Wen, Shenzhen (CN)

(73) Assignee: Siemens Healthcare GmbH, Erlangen (DE)

(*) Notice: Subject to any disclaimer, the term of this patent is extended or adjusted under 35 U.S.C. 154(b) by 52 days.

(21) Appl. No.: 17/464,087

(22) Filed: Sep. 1, 2021

(65) Prior Publication Data
US 2022/0065968 A1    Mar. 3, 2022

(30) Foreign Application Priority Data
Sep. 2, 2020  (CN) .................. 202010908566.X (51) Int. Cl.
  *G01R 33/36*   (2006.01)
  *G01R 33/567*  (2006.01)
  *A61B 5/055*   (2006.01)

(52) U.S. Cl.
  CPC .......... *G01R 33/5676* (2013.01); *A61B 5/055* (2013.01); *G01R 33/3635* (2013.01)

(58) Field of Classification Search
  CPC ............ G01R 33/5676; G01R 33/3635; G01R 33/56509; G01R 33/3415; G01R 33/365;
  (Continued)

(56) References Cited

U.S. PATENT DOCUMENTS

2007/0229080 A1  10/2007  Weiss et al.
2009/0230966 A1   9/2009  Ehnholm
(Continued)

FOREIGN PATENT DOCUMENTS

CN    1947027 A     4/2007
CN  101073017 A    11/2007
(Continued)

OTHER PUBLICATIONS

Wang Jianmin et al. "Calculation of Signal-To-Noise Ratio For Magnetic Resonance Parallel Acquisition Images" Proceedings of the First National Symposium on Brain and Cognitive Sciences, pp. 164, 2005. English translation provided.
(Continued)

*Primary Examiner* — Pascal M Bui Pho
*Assistant Examiner* — Alexei Bykhovski
(74) *Attorney, Agent, or Firm* — Banner & Witcoff Ltd.

(57) ABSTRACT

The disclosure relates to a magnetic resonance imaging device configured to exert a high-frequency electromagnetic field on an object under test in a static magnetic field and to reconstruct an image based on magnetic resonance signals. The magnetic resonance imaging device comprises a receiving coil comprising a plurality of receiving coil elements and configured to receive magnetic resonance signals and feed the magnetic resonance signals to a receiver, and a coupler configured to be coupled with at least a first receiving coil element of the receiving coil, the coupler being directionally coupled with at least the receiver, the first receiving coil element being configured to receive a high-frequency electromagnetic wave signal through the coupler. The directional coupling between the coupler and the receiver is so regulated that the first receiving coil element transmits the high-frequency electromagnetic wave signal to the object under test to sense a physiological movement signal.

11 Claims, 2 Drawing Sheets

(58) Field of Classification Search
CPC ............................ G01R 33/3621; G01R 33/34;
G01R 33/3642; A61B 5/055; A61B
5/0507; A61B 5/0816; A61B 5/0205;
A61B 5/024; A61B 5/08
See application file for complete search history.

(56) References Cited

U.S. PATENT DOCUMENTS

| | | | | |
|---|---|---|---|---|
| 2011/0084694 A1* | 4/2011 | Waffenschmidt | .. | G01R 33/3692 |
| | | | | 324/318 |
| 2015/0335268 A1* | 11/2015 | Biber | .................. | A61B 5/0535 |
| | | | | 600/411 |
| 2017/0160367 A1 | 6/2017 | Schröter et al. | | |
| 2018/0081009 A1 | 3/2018 | Duensing et al. | | |
| 2018/0353139 A1* | 12/2018 | Speier | .................. | A61B 5/725 |
| 2019/0154774 A1 | 5/2019 | Hushek et al. | | |
| 2019/0179000 A1* | 6/2019 | Adolf | ..................... | H01Q 1/362 |
| 2019/0195970 A1* | 6/2019 | Liu | ....................... | G01R 33/288 |
| 2020/0158806 A1* | 5/2020 | Okamoto | ............. | G01R 33/543 |

FOREIGN PATENT DOCUMENTS

| | | |
|---|---|---|
| CN | 102066967 A | 5/2011 |
| CN | 105078459 A | 11/2015 |
| CN | 107438772 A | 12/2017 |
| CN | 208488538 U | 2/2019 |
| CN | 111198346 A | 5/2020 |
| EP | 0306763 A2 | 3/1989 |
| EP | 3413075 A1 | 12/2018 |

OTHER PUBLICATIONS

Cao Zhiqiang et al. "Design of Dual-Coil Wireless Energy Transmission System Based On Phase Adaptation" Sensors and Microsystems, vol. 37, No. 2, pp. 102-105, 2018.

* cited by examiner

RESPIRATORY DETECTION TRANSCEIVER

CROSS-REFERENCE TO RELATED APPLICATIONS

The present application claims the benefit of the filing date of China patent application no. CN 202010908566.X, filed on Sep. 2, 2020, the contents of which are incorporated herein by reference in their entirety.

TECHNICAL FIELD

The disclosure relates to medical devices and, in particular, to a measurement arrangement and a magnetic resonance imaging device associated with respiratory movements of a patient during a magnetic resonance imaging examination.

BACKGROUND

A magnetic resonance imaging (MRI) device is an imaging device for examining the alignment of nuclei (for example, hydrogen nuclei H+) spin in a specific magnetic field, for example in an external magnetic field exerted on a uniform static magnetic field, and using an alternating magnetic field (or RF pulses) having a Larmor frequency to excite the nucleus spin to surround the aligned precession through an antenna. The attenuation of the precession or excitation of the above-mentioned aligned nuclei spin from an excited state to a small-energy state under the action of the excitation of RF pulses is measured as a magnetic resonance signal and the magnetic resonance signal is received through the antenna. The anatomic information, for example, the spatial information and type information of the nucleus constituting the above-mentioned region, of the region can be learned from an analysis of the received alternating magnetic field or magnetic resonance signal, and the accurate image information in a human body can be thereby obtained.

With the aid of a gradient magnetic field, position encoding is performed for RF pulse signals exerted on an object for radiation. Position encoding allows received signals to be associated with a voxel. Then, the received signals are analyzed and a 3-D image of the object (e.g. a person) under test is provided and examined.

A possible cause for an error or artifact during an examination of a magnetic resonance image results from movement of a patient. It takes some time to acquire a magnetic resonance image. It is important for a patient to keep in a static state during a magnetic resonance examination. However, in view of respiratory movements of the patient, it is unrealistic to keep the patient in a static state during the whole examination of the abdomen or chest. To this end, many methods for acquiring respiration-corrected magnetic resonance data of the patient have been developed. A technical solution has been proposed that respiratory data of the patient is used to trigger a measurement. For example, magnetic resonance data and respiratory data are both acquired, and respiratory data may be assessed and used to distinguish from magnetic resonance data (for example, retrospective gating) according to the respiratory phase.

SUMMARY

In view of this, in one aspect, the disclosure provides an MRI device. The MRI device is configured to exert a high-frequency electromagnetic field on an object (e.g. a person) under test in a static magnetic field, reconstruct an image based on acquired magnetic resonance signals, transmit high-frequency electromagnetic wave signals to the object under test in a static magnetic field based on multiplexing at least one receiving coil element of the receiving coil to be a high-frequency electromagnetic wave signal sending/transmitting antenna, and receive return signals of the high-frequency electromagnetic wave signals to monitor mechanical periodic physiological movement signals, for example, respiratory signals and heartbeat signals, to solve the disturbance problem caused by the design, layout and electromagnetic decoupling of the receiving coil/antenna.

The magnetic resonance imaging device comprises: a receiving coil comprising a plurality of receiving coil elements and at least configured to receive magnetic resonance signals and feed the magnetic resonance signals to a receiver, and a coupler, configured to be coupled with at least a first receiving coil element of the receiving coil, the coupler being directionally coupled with at least the receiver, and the first receiving coil element being configured to receive a high-frequency electromagnetic wave signal through the coupler, wherein the directional coupling between the coupler and the receiver is so regulated that the first receiving coil element transmits the high-frequency electromagnetic wave signal to the object under test to sense a physiological movement signal of the object under test.

Alternatively, the receiver is connected with the coupler and the receiver is configured to receive high-frequency electromagnetic wave signals returned (e.g. reflected) from the object under test, and the directional coupling between the coupler and the receiver is so regulated that the high-frequency electromagnetic wave signals coupled from the coupler to the receiver are reduced to isolate the high-frequency electromagnetic wave signals received by the receiver and the attenuation of the magnetic resonance signals returned (e.g. reflected) from the first receiving coil element and/or the return (e.g. reflected) high-frequency electromagnetic wave signals is reduced during the transmission from the coupler to the receiver.

Alternatively, the coupler has a first port receiving the high-frequency electromagnetic wave signals, a second port transmitting the high-frequency electromagnetic wave signals to the first receiving coil element, and a third port connected with the receiver.

Alternatively, the magnetic resonance imaging device further comprises a tuning control circuit disposed between the first receiving coil element and the coupler to regulate the impedance match between the first receiving coil element and the coupler.

Alternatively, the coupler and the first receiving coil element are coupled through a feed line.

Alternatively, the edge of the first receiving coil element overlaps the edge of the adjacent receiving coil element so that electromagnetic decoupling is realized between the first receiving coil element and the adjacent receiving coil element.

Alternatively, the coupler includes a directional coupler. Alternatively, the high-frequency electromagnetic wave signals transmitted by the first receiving coil element to the object under test include pilot tone signals.

One advantage of the magnetic resonance imaging device provided in the disclosure is that at least one receiving coil element of the receiving coil is multiplexed to transmit/send high-frequency electromagnetic wave signals for sensing physiological movement signals to an object under test so that the change of the design of the receiving coil antenna is small and the structure is simple.

Another advantage is that satisfactory electromagnetic decoupling is achieved between receiving coil elements of the multiplexed receiving coil, especially between receiving coil elements in the middle of the receiving coil.

A further advantage is that the directional coupling between at least one receiving coil element of the multiplexed receiving coil and the receiver can be reduced so that a carrier signal transmitted by the receiving coil element is stronger and a physiological movement signal, for example, a respiratory movement signal, is intensified or a higher signal-to-noise ratio is achieved.

Thus, the structure realizes the multiplexing of the receiving coil of the magnetic resonance imaging device to be a coil antenna transmitting a high-frequency electromagnetic signal with a sensing frequency to monitor a physiological movement signal of the object under test, and achieves advantages such as a simple structure and a high signal-to-noise ratio.

BRIEF DESCRIPTION OF THE DRAWINGS/FIGURES

The embodiments of the disclosure will be described in detail below by reference to the drawings so that those skilled in the art can have a clearer idea of the above-mentioned and other characteristics and advantages of the present disclosure.

DESCRIPTION OF REFERENCE NUMERALS IN THE DRAWINGS

100: Magnetic resonance imaging device
101: Static magnet
103: Gradient coil
105: Gradient magnetic field power supply
107: Diagnostic table
109: Sequence control unit
111: Body coil
113: Transmitter unit
1131: Oscillator
1133: First modulator
1135: Amplifier
1137: Second modulator
115: Receiving coil
1151: Receiving coil element
1152: First receiving coil element
1153: Feed line
117: Receiver
1171: Low-noise amplifier
1172: Analog-to-digital converter
119: Coupler
121: Tuning control circuit
123: Interface
125: Display
127: Storage device
129: Aperture
131: Processing circuit
1311: System control function
1313: Tuning control function
1315: Trigger pulse generation function
1317: Reconstruction function.

DETAILED DESCRIPTION

To help understand more clearly the technical characteristics, objects, and effects of the present disclosure, specific embodiments of the present disclosure are described below by reference to the drawings in which the same reference numeral represents the same part.

In a magnetic resonance imaging system, an RF signal may be transmitted to a patient/object under test/object under test, and then an alternating magnetic field signal reflected by the object excited the RF signal in the magnetic field environment may be detected/measured to detect a respiratory movement signal, for example. The transmit carrier frequency of the above-mentioned RF signal for measuring a respiratory movement signal has a frequency close to the frequency of a magnetic resonance signal, namely a Larmor frequency. Therefore, through the multiplexing of the receiving channel of the magnetic resonance imaging device, the RF signal is sent to the tissue of the patient, wherein the receiving portion at least comprises a coil antenna, a low noise amplifier (LNA), and an analog-to-digital converter.

In order to alleviate signal disturbance during magnetic resonance imaging or scanning, the physiological movement signal sensing component, which transmits an RF signal for measuring a respiratory movement signal, is arranged in the shape of a small ring to decouple with the major magnetic resonance receiving coil assembly or array. The physiological movement signal sensing component is used to sense respiratory movement signals and heart rhythm/heartbeat signals by receiving return high-frequency electromagnetic wave signals.

The decoupling mode that is usually used for the receiving coil assembly or array includes arranging adjacent receiving coil elements with their edges overlapping each other to reduce electromagnetic coupling. Here, the physiological movement signal sensing component for measuring respiratory movement signals may be placed at the overlapped part of adjacent receiving coil elements to achieve electromagnetic decoupling between the physiological movement signal sensing component and the receiving coil. However, the above-mentioned decoupling mode is valid only for adjacent receiving coil elements during a measurement, and the decoupling effect is not good for the physiological movement signal sensing component adjacent to the adjacent receiving coil elements. For this reason, the physiological movement signal sensing component is implemented smaller in size. However, this lowers the quality of the received alternating magnetic field signal associated with a physiological movement signal. In addition, more additional physiological movement signal sensing components may be implemented and arranged. However, such a structure will greatly influence the layout and design of a magnetic resonance antenna.

Figure 1:
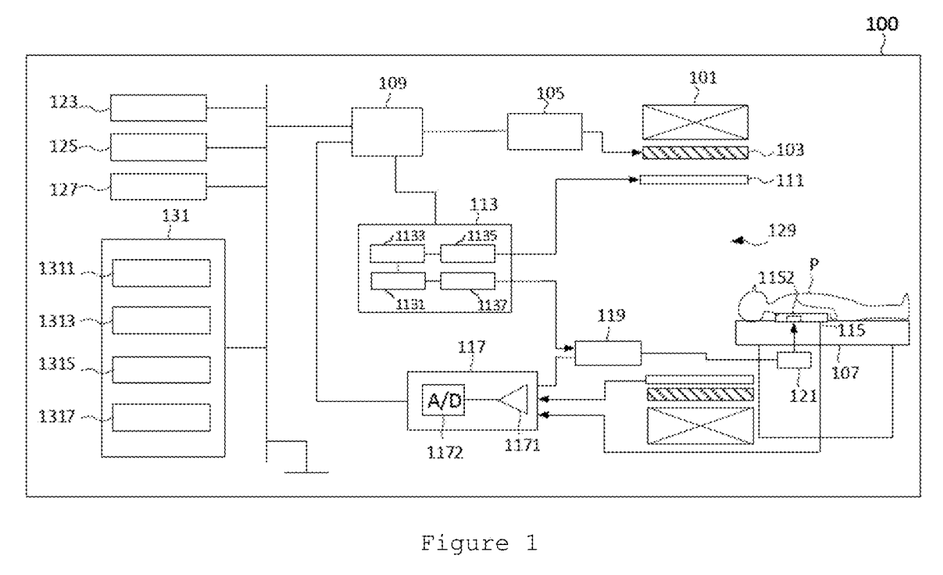
FIG. 1 shows the structure of a magnetic resonance imaging device according to one exemplary embodiment.

FIG. 1 shows the structure of the magnetic resonance imaging device 100 according to one exemplary embodiment.

As shown in FIG. 1, the magnetic resonance imaging device 100 comprises a static magnet 101, a gradient coil 103, a gradient magnetic field power supply 105, a diagnostic table 107, a sequence control unit 109 (e.g. sequence control circuitry comprising processing circuitry, software, or combinations of these), a body coil 111 (or a transmitter coil), a transmitter unit 113 (e.g. a transmitting portion or transmitting circuit comprising transmitting circuitry, software, or combinations of these), a receiving coil 115, a receiver 117 (e.g. a receiver circuit comprising receiving circuitry, software, or combinations of these), a coupler 119, and a processing circuit 131 (e.g. processing circuitry, software, or combinations of these).

The static magnet 101 provides a uniform, static magnetic field (B0 field) to align the nuclei spin in a measurement region. The static magnet 101 is usually a super conducting magnet.

The gradient coil 103 may be disposed on the inner side of the static magnet 101 and include three groups of orthogonal coils corresponding to the X-axis, Y-axis, and Z-axis, respectively. The three groups of coils of the gradient coil 103 independently receive the current provided by the gradient magnetic field power supply 105 and generate gradient fields whose magnetic field strengths vary in the X-axis, Y-axis and Z-axis, respectively.

The gradient fields generated by the gradient coil 103 with respect to the X-axis, Y-axis and Z-axis, respectively, correspond to a slice-selection gradient field, a phase-encoding gradient field, and a frequency-encoding gradient field (or readout gradient field), for example. The slice-selection gradient field is used to properly determine slices of an image. The phase-encoding gradient field is used to bring about a phase change to a magnetic resonance signal. The frequency-encoding gradient field is used to bring about a frequency change to a magnetic resonance signal.

The gradient magnetic field power supply 105 can provide a current to a gradient coil 103 under the control of the sequence control unit 109, and the current may be in the form of a pulse train to enable the gradient coil 103 to send a gradient pulse train after excitation.

The diagnostic table 107 is a device having a bed to place an object P under test. Under the control of a diagnostic table control circuit, the diagnostic table 107 guides and moves the bed carrying the object P under test into the aperture 129. The diagnostic table 107 may be placed in the examination room of the magnetic resonance imaging device 100 provided in the disclosure, with the long-side direction parallel to the central axis of the static magnet 101.

The sequence control unit 109 is used to provide a pulse train for the gradient magnetic field power supply 105 and the transmitter unit 113 so that the gradient coil 103 and the body coil 111, respectively, transmit the excitations of the gradient RF pulse (train) and the RF pulse (train) to a measurement region according to pulse trains. The sequence control unit 109 can provide a corresponding pulse train according to different examinations, type of a sequence, scanning, imaging protocol, or characteristics of an imaged tissue. Related parameters of a pulse train include current size, time sequence, amplitude, repetition time, and RF pulse (or high-frequency pulse) of the spectral power distribution.

According to the magnetic resonance imaging device 100 in an embodiment, the sequence control unit 109 can control the gradient magnetic field power supply 105, the transmitter unit 113, the duplexer, and the receiver 117 according to the sequence output by the processing circuit 131, and the physiological movement signals obtained from subsequent decoding with regard to physiological movements of the object P under test so as to carry out imaging of the object P under test.

According to the magnetic resonance imaging device 100 in an embodiment, based on physiological movement signals, the sequence control unit 109 can control the trains involved in the imaging of the object P under test who is configured in a static magnetic field and irradiated by a high-frequency/RF magnetic field. For respiratory signals of physiological movement signals, the sequence control unit 109 controls a train by using the trigger pulse generation function 1315 in the processing circuit 131 and the trigger pulses generated by respiratory signals of the object P under test. The imaging where the control of trigger pulse trains is used, equivalent to the synchronous imaging of respiratory signals of the object P under test, can not only effectively reduce disturbance and artifacts introduced by respiratory movements, but also improve the imaging efficiency.

The transmitter unit 113 comprises an oscillator 1131, a first modulator 1133, an amplifier 1135, and a second modulator 1137. Under the control of the sequence control unit 109, the transmitter unit 113 can modulate RF pulses (or high-frequency pulses) to a magnetic resonance frequency (namely, the Larmor frequency) and provide the pulses to the body coil 111. The magnetic resonance frequency can be predetermined according to the gyromagnetic ratio of an atom in the object under test in magnetic resonance imaging and the magnetic flux density of the static magnetic field B0. For example, when the magnetic flux density is 1.5 T, the magnetic resonance frequency is roughly 64 MHz. The oscillator 1131 may be considered as a crystal oscillator using an oscillator circuit having a quartz crystal unit and a frequency multiplier. The oscillator 1131 is disposed to be connected with the first modulator 1133. Under the output control of the sequence control unit 109, the oscillator 1131 outputs a signal having a first oscillation frequency, the first modulator 1133 modulates the signal having a first oscillation frequency and output by the oscillator 1131 to a magnetic resonance frequency (namely, the Larmor frequency), and further generates an RF pulse having the magnetic resonance frequency through an RF pulse waveform generator, and the first modulator 1133 provides the RF pulse (train) to the amplifier 1135 for amplification. Here, the first modulator 1133 is an RF modulator, the amplifier 1135 may be an RF amplifier, and the amplifier 1135 may be connected with at least the body coil 111 to provide the body coil with amplified RF pulses to excite the body coil 111 to generate a high-frequency magnetic field B1 orthogonal to the static magnetic field B0. Here, the amplifier 1135 may be an RF amplifier, which amplifies RF pulses having the magnetic resonance frequency to a desired amplitude.

The oscillator 1131 may be connected with the second modulator 1137. The second modulator 1137 modulates a second oscillation signal output by the oscillator 1131 to a high-frequency electromagnetic wave signal, and the high-frequency electromagnetic wave signal has a frequency of monitoring mechanical periodic physiological movement signals. The second modulator 1137 may be connected with a transmitting antenna/coil, and the high-frequency electromagnetic wave signal is irradiated to the object P under test through the transmitting antenna. According to some embodiments, an independent oscillator 1131 may be provided to provide a second oscillation signal. According to some embodiments, the high-frequency electromagnetic wave signal may be a pilot tone signal, that is to say, the second modulator 1137 can modulate the pilot tone signal. In addition, the high-frequency electromagnetic wave signal generated to monitor physiological movement signals of the object P under test may be provided by some small-signal and high-frequency signal generation circuits, for example, a direct digital synthesizer (DDS) circuit or a phase-locked loop (PLL) circuit.

The body coil 111 is an RF coil disposed on the inner side of the gradient coil 103. The body coil 111 receives RF pulses (train) provided by the transmitter unit 113 and generates a high-frequency magnetic field B1. The body coil 111 applies the high-frequency magnetic field B1 to the object P under test in a static magnetic field B0. The body coil 111 may be used as a transmitting-receiving coil, and the body coil 111 may comprise a plurality of coil elements.

The magnetic resonance imaging device 100 according to one embodiment further comprises a duplexer (not shown), and the duplexer switches over the connections between the transmitter unit 113 and the body coil 111 and between the body coil 111 and the receiving coil 115 under the control of the sequence control unit 109. That is to say, under the control of the sequence control unit 109 for the imaging sequence of the object P under test, the duplexer can switch the connected destination of the body coil 111 to the transmitter unit 113 or the receiver 117 to realize a switchover between the functions of the body coil 111 transmitting and receiving magnetic resonance signals according to the requirements of magnetic resonance imaging.

Under the control of the sequence control unit 109, the receiver 117 can generate digital magnetic resonance signals based on the magnetic resonance signals fed by the receiving coil 115 through the transmission line.

The interface 123 has a circuit or port processing various instructions and information input from the operator. For example, the interface 123 has a circuit or device associated with a directing device such as mouse or an input device such as keyboard. In addition, the circuit implemented via the interface 123 is not limited to the circuit associated with a physical operation component such as mouse or keyboard. For example, the interface 123 may also have an electrical signal processing circuit, and the electrical signal processing circuit/portion receives corresponding electrical signals of input operations from an external input device provided independently of the magnetic resonance imaging device 100, and outputs the received electrical signals to various circuits.

In addition, under the control of the processing circuit 131, the interface 123 acquires various data from an external storage device, modality device, or radiology information system (RIS) connected via a network or directly connected.

Under the control of the system control function 1311 of the processing circuit 131, the display 125 displays the magnetic resonance image generated by the reconstruction function 1319, various information associated with imaging and image processing, and returns high-frequency electromagnetic wave signals separated and obtained at the receiver 117, for example, phase change of pilot tone signals, and obtains physiological movement signals, such as respiratory signals/respiratory movement signals therefrom. The display 125 is, for example, a cathode-ray tube (CRT) display, a liquid crystal display (LCD), an organic electro-luminescence (EL) display, a light-emitting diode (LED) display or any other suitable display device, including those known in the art.

The storage device 127 stores the magnetic resonance data filled by the reconstruction function 1317 into k-space and the data of the magnetic resonance image generated by the reconstruction function 1317. The storage device 127 may store various sequences, including the conditions containing a plurality of imaging parameters for stipulating an imaging sequence. The storage device 127 stores the programs involved in various reconstruction methods used in the reconstruction function. In addition, the storage device 127 stores corresponding programs (e.g. computer-readable and executable instructions or code) of various functions executed in the processing circuit 131. The storage device 127 is, for example, a non-transitory computer-readable medium such as a random access memory (RAM), a semiconductor memory such as flash memory, a hard disk drive, a solid state disk drive, or an optical disk. In addition, the storage device 127 may also be a driving device reading and writing various information between a CD-ROM drive, a DVD drive, a flash memory, and portable storage media.

The processing circuit 131 has hardware resources such as a processor, a read-only memory (ROM), a random access memory (RAM), and other memories (not shown), and the processing circuit 131 uniformly controls the magnetic resonance imaging device 100 as described herein. The processing circuit 131 has a system control function 1311, a trigger pulse generation function 1313, a tuning control function 1315, and a reconstruction function 1317. These functions are stored in the form of computer-executable programs (e.g. instructions or code) in the storage device 127. The processing circuit 131 may be implemented as a processor or suitable processing circuitry configured to read the corresponding programs of these functions from the storage device 127 and execute the programs to implement their respective corresponding functions.

In addition, a plurality of independent processors may also be combined to form the processing circuit 131, and these independent processors may execute programs to implement their respective functions. In other words, the above-mentioned functions may be configured to be programs, and a processor executes the programs, or specific functions may be installed in a dedicated, independent program-executing circuit, processing circuitry, hardware, etc. Furthermore, the system control function 1311, the tuning control function 1313, the trigger pulse generation function 1315, and the reconstruction function 1317 of the processing circuit 131 are an example of the system control portion/unit, the tuning portion, the trigger pulse generation portion, and the reconstruction portion, respectively.

The processor may be implemented, for example, as a central processing unit (CPU), a graphics processing unit (GPU), an application specific integrated circuit (ASIC), a programmable logic device (for example, simple programmable logic device (SPLD)), a complex programmable logic device (CPLD), a field programmable gate array (FPGA), etc.

The processor implements various functions by reading the programs stored in the storage device 127 and executing them. In addition, programs may also be directly installed in the circuits of the processor, instead of being stored in the storage device 127. In this case, the processor implements the functions by reading the programs in the circuits and executing them. Furthermore, the diagnostic control circuit, the transmitter unit 113, the receiver 117, and the sequence control circuit 109 may also be electronic circuits of the above-mentioned processor.

The processing circuit 131 uniformly controls the magnetic resonance imaging device 100 through the system control function 1311. Specifically, the processing circuit 131 reads the system control programs stored in the storage device 127, expands the programs in the storage, and controls various circuits of the magnetic resonance imaging device 100 according to the expanded system control programs. For example, through the system control function 1311, the processing circuit 131 reads out the sequences about imaging from the storage device 127 based on the imaging conditions input by the operator via the interface 123. The processing circuit 131 may also generate imaging sequences based on the shooting conditions. The processing circuit 131 transmits an imaging sequence to the sequence control unit 109, and the sequence control unit 109 generates an RF pulse train thereby to control the imaging of the object P under test.

Through the reconstruction function 1317, the processing circuit 131 fills magnetic resonance data in k-space in the read-out direction, for example, according to the strength of the gradient magnetic field. The processing circuit 131 has a calculation function and generates a magnetic resonance image by performing a (inverse) Fourier transform for the (digital) magnetic resonance data filled in the K-space. In addition, the generation of a magnetic resonance image is not limited to the above-mentioned sequence. The parallel imaging and compressed sensing detection may also be used to reconstruct a magnetic resonance image through the regularization of magnetic resonance data of accompanying missing (sparse) data, and a deep neural network obtained by learning and training the magnetic resonance data of the accompanying missing (sparse) data may be used to implement the image reconstruction. The processing circuit 131 outputs the magnetic resonance image to the display 125 and the storage device 127.

The overall structure of the magnetic resonance imaging device 100 in the present implementation mode is described above. The specific structures of the receiving coil 115 multiplexed to be a coil antenna transmitting high-frequency electromagnetic wave signals for sensing physiological movement signals, and the receiver 117 multiplexed to receive return high-frequency electromagnetic wave signals to obtain physiological movement signals will be described below.

Figure 2:
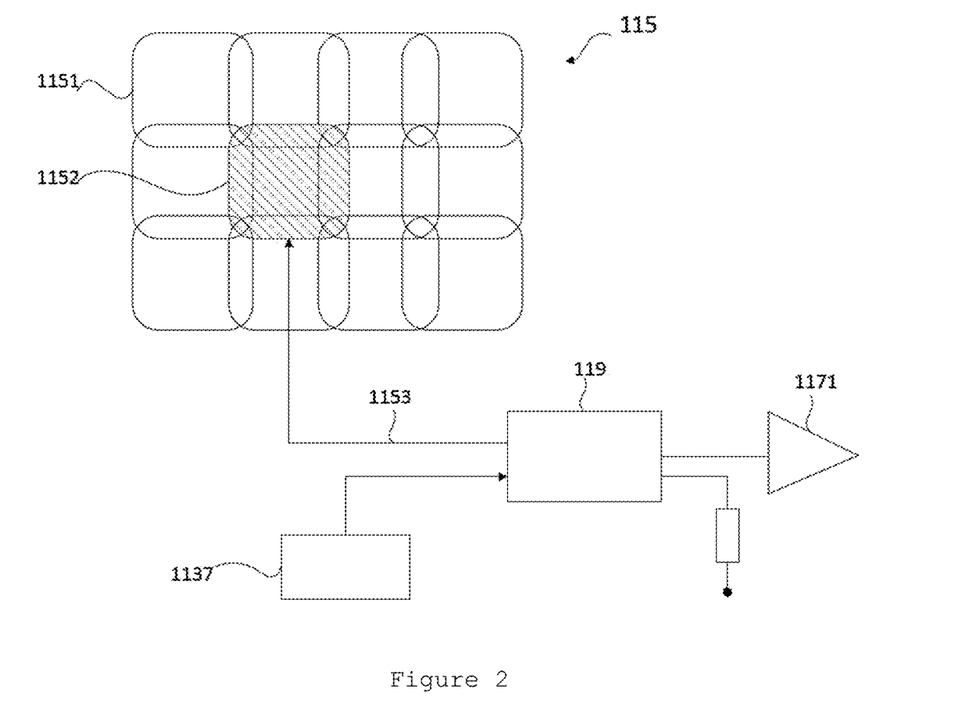
FIG. 2 shows the structure of a receiving coil multiplexed to sense physiological movement signals according to one exemplary embodiment.

FIG. 2 shows the structure of the receiving coil 115 multiplexed to sense physiological movement signals according to one exemplary embodiment.

The receiving coil 115 may include an RF coil and is disposed on the inner side of the gradient coil 103, and is further disposed close to the object P under test. The receiving coil 115 is used to receive magnetic resonance signals reflected by the object P under test from the high-frequency electromagnetic field exerted on the object P under test during imaging. The receiving coil 115 outputs the magnetic resonance signals to the receiver 117.

As shown in FIG. 2, the receiving coil 115 may consist of a coil array, namely, a plurality of receiving coil elements 1151. The receiving coil 115 may be disposed as local coils at the near end of the object P under test, for example, as a spine coil mounted in the position of the bed of the diagnostic table 107, and an abdomen coil and a chest coil covering the abdomen and the chest of the object P under test, respectively. The above-mentioned local coils are used to receive magnetic resonance signals from corresponding anatomical positions. Since local coils are close to the corresponding anatomical positions, local coils, for example, the abdomen coil, the spine coil and the chest coil, may be used to monitor some important visceral organs producing mechanical physiological movement signals, such as heart and lungs, and a high signal-to-noise ratio may be achieved. The receiver 117 may comprise a low-noise amplifier (LNA) 1171 configured to amplify the magnetic resonance signals output from the receiving coil 115, and an analog-to-digital converter 1172 configured to convert the analog magnetic resonance signals output from the receiving coil 115 into digital magnetic resonance signals. FIG. 2 shows the suppression of electromagnetic coupling by arranging relative positions between receiving coil elements 1151 of the receiving coil 115, namely electromagnetic decoupling by overlapping the edges of adjacent receiving coil elements 1151, or partially overlapping each other.

In some embodiments, the receiving coil 115 may be implemented as a transmitting-receiving coil, and the receiving coil 115 transmits a high-frequency magnetic field to the object P under test under the excitation of a high-frequency signal (RF signal). The receiving coil may be implemented as a transmitting-receiving coil, and the receiving coil 115 may also be configured to send high-frequency electromagnetic wave signals (high-frequency signals/RF signals) with a sensing frequency to visceral organs, which reflect mechanical periodic physiological movement signals of the object P under test, and generate return high-frequency electromagnetic wave signals containing physiological information of these mechanical movements.

Based on the multiplexed receiving coil 115 sending high-frequency electromagnetic wave signals with a sensing frequency to visceral organs, which reflect mechanical periodic physiological movement signals of the object P under test, the magnetic resonance imaging device 100 is configured to monitor physiological movement signals of the object P under test, for example respiratory signals and heartbeat signals. The magnetic resonance imaging device 100 in an embodiment comprises: a receiving coil 115 comprising a plurality of receiving coil elements 1151, and at least configured to receive magnetic resonance signals and feed the magnetic resonance signals to a receiver 117, and a coupler 119 configured to be coupled with at least a first receiving coil element 1152 of the receiving coil 115, the coupler 119 being directionally coupled with at least the receiver 117, and the first receiving coil element 1152 being configured to receive a high-frequency electromagnetic wave signal through the coupler 119, wherein the directional coupling between the coupler 119 and the receiver 117 is so regulated that the first receiving coil element 1152 transmits the high-frequency electromagnetic wave signal to the object P under test to sense a physiological movement signal of the object P under test. Here, the first receiving coil element 1152 serves as a sensing coil monitoring physiological movement signals, and the coupler 119 may also include a directional coupler.

Here, the high-frequency electromagnetic wave signals transmitted by the first receiving coil element 1152 to the object P under test to monitor physiological movement signals may be continuous or discontinuous, depending on the requirements for magnetic resonance imaging and the part involved in the magnetic resonance imaging. Here, the first receiving coil element 1152 may be located in the middle of the receiving coil 115, and electromagnetic decoupling is achieved between the first receiving coil element and surrounding receiving coil elements 1151 by partially overlapping the first receiving coil element 1152 and surrounding receiving coil elements 1151, or overlapping the edges. Here, a high electromagnetic decoupling performance can also be achieved between the first receiving coil element 1152 and the non-adjacent receiving coil element 1151. In addition, according to some embodiments the high-frequency electromagnetic wave signals transmitted by the first receiving coil element 1152 to the object P under test include pilot tone signals.

Here, the first receiving coil element 1152 may have a matching circuit (not shown), which has a variable capacitor. Under the control of the tuning control function 1313, the matching circuit can change the direct capacitance of the variable capacitor according to the frequency of the high-frequency electromagnetic wave signal transmitted by the first receiving coil element 1152 so as to achieve a matching between the sensitivity of the first receiving coil element 1152 and the frequency of the high-frequency electromagnetic wave signal.

Here, the first receiving coil element 1152 may be connected with the transmitter unit 113 through the coupler 119, the second modulator 1137 modulates the oscillation signal fed by the oscillator 1131 to a high-frequency electromagnetic wave signal, the high-frequency electromagnetic wave signal is fed to the first receiving coil element 1152 through the coupler 119, the first receiving coil element 1152 irradiates the high-frequency electromagnetic wave signal to the monitored visceral organs of the object P under test, and the receiving coil 115 receives the high-frequency electromagnetic wave signal returned from the object P under test. Hereby, an amplitude change and/or phase shift caused by mechanical periodic movements of the body or visceral organs of the object P under test can be extracted from the received high-frequency electromagnetic wave signal.

For this reason, the oscillator 1131 may generate a proper high-frequency signal so that the frequency of the high-frequency electromagnetic wave may be located around the Larmor frequency or within the Larmor frequency. The second modulator 1137 may be designed to modulate the high-frequency electromagnetic wave signal using codes. Codes are so designed that the high-frequency electromagnetic wave signals can be uniquely distinguished from other high-frequency signals, for example magnetic resonance signals, in image acquisition of the magnetic resonance imaging device. Codes may be designed to encode the phase of modulated high-frequency electromagnetic wave signals so that the phase shift caused by transmission and mechanical physiological movements of the object P under test can be detected when the receiver 117 receives the high-frequency electromagnetic wave signals.

According to an embodiment, the second modulator 1137 can modulate the oscillation signal fed by the oscillator 1131 into a pilot tone signal, thus the first receiving coil element 1152 irradiates the pilot tone signal to the monitored visceral organ of the object P under test through the directional coupling of the coupler 119, and thus the receiving coil 115 receives the pilot tone signal returned from the object P under test.

In addition, when the first receiving coil element 1152 continuously transmits high-frequency electromagnetic wave signals for monitoring physiological movement signals to the object P under test, magnetic resonance signals are simultaneously collected. Thus, the separation of magnetic resonance signals from high-frequency electromagnetic wave signals for monitoring physiological movement signals at the receiver 117 should be considered so that the return high-frequency electromagnetic wave signals can be obtained through further processing and analysis. Here, the second modulator 1137 can be utilized to design the high-frequency electromagnetic wave signals to be orthogonal to the magnetic resonance signals so that the orthogonal high-frequency electromagnetic wave signals and the magnetic resonance signals have few or no interactions. Thus, the monitoring of physiological movement signals/movements by using the high-frequency electromagnetic wave signals and the image acquisition by using magnetic resonance signals do not interfere with each other. By modulating the high-frequency electromagnetic wave signals to be orthogonal to the magnetic resonance signals, the high-frequency electromagnetic wave signals occupy different frequencies or phases from the expected magnetic resonance signals in k-space, so that they are separated when the storage device 127 fills data in k-space via the reconstruction function 1317. Thus, for each pulse train, the return high-frequency electromagnetic wave signals in k-space are determined again.

Signals not intersecting in k-space enable the high-frequency electromagnetic wave signals to be transmitted and analyzed in a favorable manner during the whole sequence, and the magnetic resonance signals for image analysis will not be interfered with.

In addition, the first receiving coil element 1152 discontinuously transmits high-frequency electromagnetic wave signals for monitoring physiological movement signals to the object P under test. The high-frequency electromagnetic wave signals may be orthogonal to the magnetic resonance signals in time so that the high-frequency electromagnetic wave signals may be temporarily interrupted or attenuated during the period the magnetic resonance signals are received. In addition, the interleaving of high-frequency electromagnetic wave signals and pulse trains in time in a favorable manner realizes the parallel acquisition of images and physiological movement signals/physiological parameters when there is no interference.

In another implementation mode, orthogonality may be provided on the side of the receiver 117. The receiver 117 may have a filter, which filters out the return high-frequency electromagnetic wave signals for monitoring physiological movements from the received return signals. For example, in the case of the orthogonality of k-space, the filter may be implemented through the selection in k-space and a Fourier transform. In the case of time orthogonality, the filter may be implemented through a corresponding time weight. For example, the filter may be implemented by performing encoding with the aid of pseudo-random codes or performing encoding with the aid of a similar template multiplied by a non-weighted template, so that pseudo-random codes can be identified at the receiver 117. Here, high-frequency electromagnetic wave signals and magnetic resonance signals may be separated based on the scalar product zero of high-frequency electromagnetic wave signals and magnetic resonance signals.

According to some embodiments, the coupler 119 is coupled with the first receiving coil element 1152 through a feed line 1153. Here, the feed line 1153 may be in the form of a cable, and the coupling between the coupler 119 and the first receiving coil element 1152 may be realized in a wireless transmission mode.

Here, when the first receiving coil element 1152 transmits a high-frequency electromagnetic wave signal, the strength of the carrier signal is intensified to obtain a better signal-to-noise ratio. According to some embodiments, the receiver 117 is connected with the coupler 119 and the receiver 117 is further configured to receive high-frequency electromagnetic wave signals returned from the object P under test, and the directional coupling between the coupler 119 and the receiver 117 is so regulated that the high-frequency electromagnetic signals coupled from the coupler 119 to the receiver 117 are reduced to isolate the high-frequency electromagnetic wave signals received by the receiver 117, and the attenuation of the magnetic resonance signals returned from the first receiving coil element 1152 and/or the return high-frequency electromagnetic wave signal during the transmission from the coupler 119 to the receiver 117 is reduced, that is to say, the magnetic resonance signals received from and/or high-frequency electromagnetic wave signals returned from the first receiving coil element 1152 may be directly transmitted to the receiver 117. Here, by regulating the directional coupling between the coupler 119 and the receiver 117, the high-frequency electromagnetic wave signals coupled from the coupler 119 to the receiver 117 may be reduced to a minimum value, and the attenuation of magnetic resonance signals transmitted from the first receiving coil element 1152 to the receiver 117 and/or return high-frequency electromagnetic wave signals may be reduced to a minimum value, namely the attenuation is close to zero.

It should be noted that the reduction of the directional coupling of the high-frequency electromagnetic wave signals between the coupler and the receiver 117 enables the first receiving coil element 1152 to receive high-frequency electromagnetic wave signals through the coupler 119 and serve as a transmitting coil/antenna of the high-frequency electromagnetic wave signal, and thus the strength of the carrier signals is intensified when the first receiving coil element 1152 transmits high-frequency electromagnetic wave signals. Here, the coupler 119 may be connected to a low-noise amplifier 1171 so that the low-noise amplifier 1171 can receive high-frequency electromagnetic wave signals returned from the first receiving coil element 1152, and the return high-frequency electromagnetic wave signals contain physiological movement signals of the object P under test.

Here, it should be noted that the receiver 117 may receive high-frequency electromagnetic wave signals returned by the object P under test according to the following paths. That is to say, the return high-frequency electromagnetic wave signals and magnetic resonance signals are fed by a plurality of receiving coil elements 1151 to the receiver 117. The other path is from the first receiving coil element 1152 and the coupler 119. An impedance match exists between the first receiving coil element and the coupler, and the mechanical periodic movements of the object P under test causes the impedance between them to change. Thus, the receiver 117 may receive another part of return high-frequency electromagnetic wave signals through the path from the first receiving coil element 1152 and the coupler 119.

Figure 3:
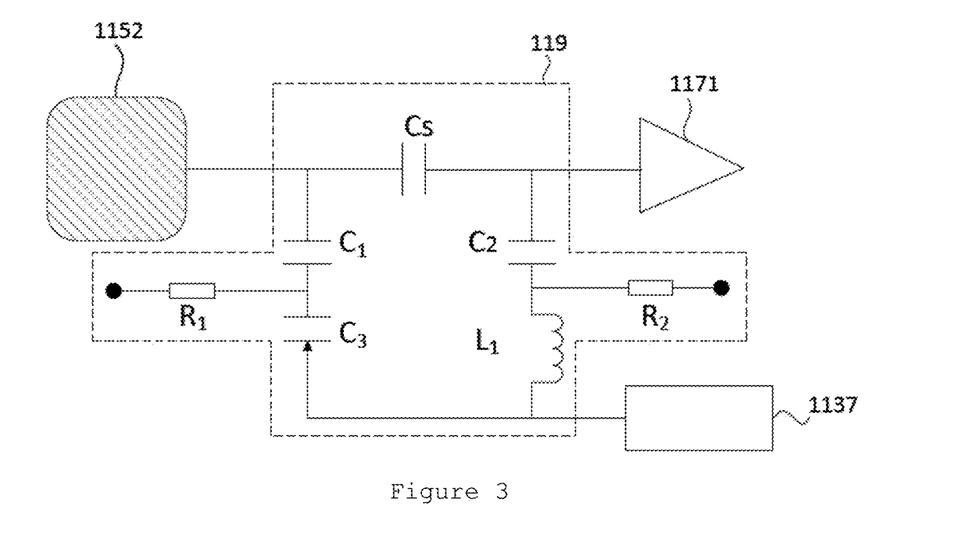
FIG. 3 shows the connections of a coupler comprising lumped elements with a first receiving coil element and a low-noise amplifier.

According to an embodiment, as shown in FIG. 3, the coupler 119 may be implemented based on lumped elements, capacitors Cs are connected in series between the first receiving coil element 1152 and the receiver 117, and the directional coupling between the coupler 119 and the receiver 117 is regulated by regulating the ratios between C1/C2/C3, the value of the inductor L1, and the ratio between the resistors R1/R2 in the coupler 119 so that the directional coupling of high-frequency electromagnetic wave signals input to the receiver 117 or the low-noise amplifier 1171 is eliminated. The coupler 119 has a small size and eddy current. In addition, an improvised directional coupler 119 may further be implemented by coupler cables. However, such a directional coupler may be implemented on a large printed circuit board and an eddy current will be introduced.

According to some embodiments, the coupler 119 has a first port receiving the high-frequency electromagnetic wave signals, a second port transmitting the high-frequency electromagnetic wave signals to the first receiving coil element 1152, and a third port connected with the receiver 117. Here, the coupler 119 receives high-frequency electromagnetic wave signals from the second modulator 1137. In addition, the coupler 119 further has a fourth port for connecting a matched load.

According to some embodiments, as shown in FIG. 2, the edges of the first receiving coil element 1152 overlap or partially overlap the edges of the adjacent receiving coil elements 1151 so that electromagnetic decoupling is achieved between the first receiving coil element 1152 and adjacent receiving coil elements 1151. Here, the first receiving coil element 1152 may be selectively located in the middle of the receiving coil 115.

According to some embodiments, the magnetic resonance imaging device 100 further comprises a tuning control circuit 121 disposed between the first receiving coil element 1152 and the coupler 119. The impedance match between the first receiving coil element 1152 and the coupler 119 is so regulated that the first receiving coil element 1152 is coupled with the coupler 119. Here, mechanical periodic physiological movements of the object P under test will cause the impedance between the first receiving coil element 1152 and the coupler 119 to change so that an impedance mismatch between the first receiving coil element 1152 and the coupler 119 will be introduced. As a result, some high-frequency electromagnetic wave signals transmitted from the first receiving coil element 1152 to the object P under test to monitor physiological movements of the object under test may be received by the receiver 117 because of the impedance mismatch between the first receiving coil element 1152 and the coupler 119. For example, the output end of the low-noise amplifier 1171 of the receiver 117 may contain return (reflected) high-frequency electromagnetic wave signals. Here, by analyzing the phase change of the high-frequency electromagnetic wave signals returned from the object P under test, physiological movement signals, including respiratory signals and/or heartbeat signals may be detected.

Here, the processing circuit 131 may control the tuning control circuit 121 through the tuning control function 1313 so as to achieve an impedance match between the first receiving coil element 1152 and the coupler 119.

On the basis of the multiplexing of the first receiving coil element 1152 to transmit high-frequency electromagnetic wave signals for monitoring physiological movement signals of the object P under test and the impedance mismatch between the first receiving coil element 1152 and the coupler 119 because of respiratory movements or heartbeats of the object P under test, the receiver 117 will receive some return high-frequency electromagnetic wave signals. In a corresponding test where only the first receiving coil element 1152 is multiplexed and respiratory movements are involved, the modulation depth of respiratory signals is up to 5.6%. However, compared with a conventional transmission mode, where a small sensing component or an impedance change, for example, is utilized, the modulation depth is only a few thousandths. In addition, the change of the base line of the received signals (for example, return high-frequency electromagnetic wave signals received by the receiver 117) is very small so that the sensitivity to interference during a magnetic resonance scan is lower.

It should be understood that although the disclosure gives a description by example embodiments, and this does not mean that each embodiment contains only one independent technical solution. The description method in the disclosure is for the sake of clarity. Those skilled in the art should consider the disclosure as an integral body. The technical solutions in all these embodiments may be combined properly to form other embodiments that those skilled in the art can understand.

The above-mentioned embodiments are preferred embodiments of the present disclosure, but are not used to limit the present disclosure. Without departing from the spirit and principle of the present disclosure, modifications, equivalent replacements, and improvements should all fall within the scope of protection of the present disclosure.

In this document, "schematic" means "acting as an instance, example, or illustration," and any schematic illustration or embodiment described in this document should not be interpreted as a more preferred or advantageous technical solution.

For ease of understanding and clarity of the drawings, only the parts related to the present disclosure are shown for a schematic purpose, and they do not represent actual structures of a product. In addition, only one of the components which have the same structure or function is depicted or marked for a schematic purpose in some drawings so that the drawings are simplified to help to understand.

In this document, "one" not only represents "only one," but also may represent "more than one." In this document, "first" and "second" are used only to distinguish from each other, but do not represent their importance or sequence, or a prerequisite for their mutual existence.

What is claimed is:

1. A magnetic resonance imaging (MRI) device configured to exert a high-frequency electromagnetic field on an object under test in a static magnetic field, and to reconstruct an image based on acquired magnetic resonance signals, the MRI device comprising:
   a receiving coil comprising a plurality of receiving coil elements, the receiving coil being configured to receive magnetic resonance signals and to couple the magnetic resonance signals to a receiver; and
   a coupler configured to be coupled with at least a first receiving coil element of the plurality of receiving coil elements of the receiving coil, the coupler being directionally coupled with the receiver, and the first receiving coil element being configured to receive a high-frequency electromagnetic wave signal through the coupler,
   wherein the receiver is connected to the coupler, the receiver being configured to receive high-frequency electromagnetic wave signals reflected from the object under test, and
   wherein a directional coupling between the coupler and the receiver is regulated (i) such that the first receiving coil element transmits the high-frequency electromagnetic wave signal to the object under test to detect a physiological movement signal of the object under test, and (ii) to reduce an attenuation of reflected high-frequency electromagnetic wave signals received by the first receiving coil element during a transmission from the coupler to the receiver.

2. The MRI device according to claim 1, wherein
   the directional coupling between the coupler and the receiver is regulated such that the high-frequency electromagnetic wave signals coupled from the coupler to the receiver are reduced to isolate the high-frequency electromagnetic wave signals received by the receiver.

3. The MRI device according to claim 2, wherein the coupler has a first port configured to receive the high-frequency electromagnetic wave signals, a second port configured to transmit the high-frequency electromagnetic wave signals to the first receiving coil element, and a third port connected to the receiver.

4. The MRI device according to claim 1, wherein
   the directional coupling between the coupler and the receiver is regulated to reduce an attenuation of high-frequency electromagnetic wave signals received by the first receiving coil element during a transmission from the coupler to the receiver.

5. The MRI device according to claim 4, wherein the coupler has a first port configured to receive the high-frequency electromagnetic wave signals, a second port configured to transmit the high-frequency electromagnetic wave signals to the first receiving coil element, and a third port connected to the receiver.

6. The MRI device according to claim 1, wherein the coupler has a first port configured to receive the high-frequency electromagnetic wave signals, a second port configured to transmit the high-frequency electromagnetic wave signals to the first receiving coil element, and a third port connected to the receiver.

7. The MRI device according to claim 1, further comprising:
   a tuning control circuit disposed between the first receiving coil element and the coupler, the tuning control circuit being configured to regulate an impedance match between the first receiving coil element and the coupler.

8. The MRI device according to claim 1, wherein the coupler and the first receiving coil element are connected to one another via a feed line.

9. The MRI device according to claim 1, wherein an edge of the first receiving coil element overlaps an edge of an adjacent receiving coil element from among the plurality of receiving coil elements such that an electromagnetic decoupling is realized between the first receiving coil element and the adjacent receiving coil element.

10. The MRI device according to claim 1, wherein the coupler comprises a directional coupler.

11. The MRI device according to claim 1, wherein the high-frequency electromagnetic wave signals transmitted by the first receiving coil element to the object under test include pilot tone signals.

* * * * *